United States Patent
Wang et al.

(10) Patent No.: US 11,339,401 B2
(45) Date of Patent: May 24, 2022

(54) GENE FOR CONTROLLING ERECTNESS GROWTH OF RICE LEAF BLADES AND APPLICATION THEREOF

(71) Applicant: Huazhong Agricultural University, Hubei (CN)

(72) Inventors: Xuelu Wang, Wuhan (CN); Shiyong Sun, Wuhan (CN)

(73) Assignee: Huazhong Agricultural University, Wuhan (CN)

( * ) Notice: Subject to any disclaimer, the term of this patent is extended or adjusted under 35 U.S.C. 154(b) by 0 days.

(21) Appl. No.: 16/803,915

(22) Filed: Feb. 27, 2020

(65) Prior Publication Data

US 2020/0199611 A1 Jun. 25, 2020

Related U.S. Application Data

(63) Continuation of application No. 15/798,384, filed on Oct. 30, 2017, now abandoned, which is a continuation of application No. PCT/CN2016/080098, filed on Apr. 23, 2016.

(30) Foreign Application Priority Data

Apr. 29, 2015 (CN) .......................... 201510219253.2

(51) Int. Cl.
*C12N 15/82* (2006.01)
*C07K 14/415* (2006.01)

(52) U.S. Cl.
CPC ........ *C12N 15/8262* (2013.01); *C07K 14/415* (2013.01); *C12N 15/8225* (2013.01); *C12N 15/8261* (2013.01); *Y02A 40/146* (2018.01)

(58) Field of Classification Search
None
See application file for complete search history.

(56) References Cited

U.S. PATENT DOCUMENTS 9,150,875 B2 * 10/2015 Han .................... C12N 15/8261

OTHER PUBLICATIONS

Dokuritsu et al., Sequence Accession AQD16322, Jun. 12, 2008, sequence alignment attached to the office action (Year: 2008).*
Deng, Minjuan et al., "OsCYCP1; 1, a PHO80 homologous protein, negatively regulates phosphate starvation signaling in the roots of rice (*Oryza sativa* L.)," Plant Molecular Biology, vol. 86, No. 6, pp. 655-669 (Dec. 31, 2014).
"RecName: FULL=Cy1; .P4.clin Short=CycP4; 1" GenBank Accession No. Q7XC35 (Apr. 1, 2015). See amino acid sequences.
"Cyclin, N-terminal domain containing protein, expressed [*Oryza sativa* Japonica Group]," GenBank Accession No. AAP55040, (May 5, 2011). See amino acid sequences.
"*Oryza sativa* Japonica Group cDNA clone: 002-129-G08, full insert sequence" GenBank Accession No. AK107529, (Dec. 4, 2008). See amino acids and nucleotide sequence at positions from 42 to 680.
"*Oryza sativa* chromosome 10 BAC OSJNBa0027P10 genomic sequence, complete sequence" GenBank Accession No. AC084763 (Aug. 29, 2001). See amino acids and nucleotide sequences.
Zhang, Keqin et al., "Genetic Dissection of Flag Leave Angle and Main Panicle Yield Trais in Rice," Chinese Agricultural Science Bulletin vol. 24, No. 9, pp. 186-192 (Sep. 2008).
Xingming Hu et al., "U-Box E3 Ubiquitin Ligase TUD1 Functions with a Hetero-trimeric G a Subunit to Regulate Brassinosteroid-Mediated Growth in Rice," PLOS Genetics, vol. 9, No. 3, e1003391, pp. 1-13 (Mar. 2013).
Asako Shimada et al., "The rice SPINDLY gene functions as a negative regulator of gibberellin signaling by controlling the suppressive function of the DELLA protein, SLR1, and modulating brassinosteroid synthesis," Plant Journal 48, pp. 390-402 (2006).
Zhi Hong et al., "The Rice brassinosteroid-deficient dwarf2 Mutant, Defective in the Rice Homolog of *Arabidopsis* DIMTNUTO/DWARF1, Is Rescued by the Endogenously Accumulated Alternative Bioactive Brassinosteroid, Dolichosterone," Plant Cell, vol. 17, pp. 2243-2254 (Aug. 2005).
Zhao et al., "Studies on the Rice Leaf Inclination1 (LC1), an IAA-amido Synthetase, Reveal the Effects of Auxin in Leaf Inclination Control," Molecular Plant, vol. 6, No. 1, pp. 174 187 (Jan. 2013).
Shu-Qing Zhao et al., "Rice leaf inclination2, a VIN3-like protein, regulates leaf angle through modulating cell division of the collar," Cell Research, vol. 20, pp. 935-947 (2010).
Yoichi Morinaka et al., "Morphological Alteration Caused by Brassinosteroid Insensitivity Increases the Biomass and Grain Production of Rice," Plant Physiology, vol. 141, pp. 924-931 (Jul. 2006).
Chizuko Yamamuro et al., "Loss of Function of a Rice *brassinosteroid insensitive1* Homolog Prevents Internode Elongation and Bending of the Lamina Joint," Plant Cell, vol. 12, pp. 1591-1605 (Sep. 2000).
Wu, Xinru et al., "Loose Plant Architecture1, an Indeterminate Domain Protein Involved in Shoot Gravitropism, Regulates Plant Architecture in Rice," Plant Physiology, vol. 161, pp. 317-329 (Jan. 2013).

(Continued)

*Primary Examiner* — Elizabeth F McElwain
(74) *Attorney, Agent, or Firm* — Mei & Mark LLP; Manni Li

(57) ABSTRACT

A method for controlling the building of architecture of gramineous crops and application thereof. The gene CYC U4;1 (Os10g41430) has a specific expression in a rice pulvinus (which is believed to have a specific expression in other gramineous crops), with a CDS sequence as shown in SEQ ID NO: 2, and an encoded amino acid sequence as shown in SEQ ID NO: 3. Also a promoter sequence of the gene, with the sequence as shown in SEQ ID NO: 1. Transgenic lines obtained by cloning a promoter and fulllength CDS of CYC U4;1 to pCAMBIA1301 and transferring this into rice Nipponbare are all characterized by having smaller leaf-stem angles than those of wild rice, accordingly, the expression level of the gene CYC U4;1 can be increased or decreased with genetic engineering technology to control the plant architecture development, thereby improving the plant architecture and increasing the density of germplasm.

8 Claims, 4 Drawing Sheets

Specification includes a Sequence Listing.

(56) References Cited

OTHER PUBLICATIONS

Jing Ning et al., "Increased Leaf Angle1, a Raf-Like MAPKKK That Interacts with a Nuclear Protein Family, Regulates Mechanical Tissue Formation in the Lamina Joint of Rice," Plant Cell, vol. 23, pp. 4334-4347 (Dec. 2011).
Ming-Yi Bai et al., "Functions of OsBZR1 and 14-3-3 proteins in brassinosteroid signaling in rice," PNAS, vol. 104, No. 34, pp. 13839-13844 (Aug. 21, 2007).
Katsuyuki Oki et al., "Function of a subunit of heterotrimeric G protein in brassinosteroid response of rice plants," Plant Signaling & Behavior, vol. 4, No. 2, pp. 126-128 (Feb. 2009).
Tomoaki Sakamoto et al., "Erect leaves caused by brassinosteroid deficiency increase biomass production and grain yield in rice," Nature Biotechnology, vol. 24, No. 1, pp. 105-109 (Jan. 2006).
Thomas R. Sinclair et al., "Erect Leaves and Photosynthesis in Rice," Science, vol. 283, No. 5407, p. 1455 (Mar. 1999).
Dan Li et al., "Engineering OsBAK1 gene as a molecular tool to improve rice architecture for high yield," Plant Biotechnology Journal, vol. 7, pp. 791-806 (2009).
Cui Zhang et al., "Dynamics of Brassinosteroid Response Modulated by Negative Regulator LIC in Rice," PLOS Genetics, vol. 8, Issue No. 4, e1002686, pp. 1-14 (Apr. 2012).
Hongning Tong et al., "Dwarf and Low-Tillering Acts as a Direct Downstream Target of a GSK3/SHAGGY-Like Kinase to Mediate Brassinosteroid Responses in Rice," Plant Cell, vol. 24: 2562-2577 (Jun. 2012).
Song, Yaling et al., "Characterization of OsIAA1 gene, a member of rice Aux/IAA family involved in auxin and brassinosteroid hormone responses and plant morphogenesis," Plant Mol. Biol., No. 70, pp. 297-309 (2009).
Li-Ying Zhang et al., "Antagonistic HLH/bHLH Transcription Factors Mediate Brassinosteroid Regulation of Cell Elongation and Plant Development in Rice and *Arabidopsis*," Plant Cell, vol. 21, pp. 3767-3780 (Dec. 2009).
Zhi Hong et al., "A Rice Brassinosteroid-Deficient Mutant, *ebisu dwar* (d2), Is Caused by a Loss of Function of a New Member of Cytochrome P450," Plant Cell, vol. 15, pp. 2900-2910 (Dec. 2003).
Sumiyo Tanabe et al., "A Novel Cytochrome P450 Is Implicated in Brassinosteroid Biosynthesis via the Characterization of a Rice Dwarf Mutant, dwarf11, with Reduced Seed Length," Plant Cell, vol. 17, pp. 776-790 (Mar. 2005).
Hui Li et al., "A comprehensive genetic study reveals a crucial role of CYP90D2/D2 in regulating plant architecture in rice (*Oryza sativa*)," New Phytologist, vol. 200, pp. 1076-1088 (2013).
Zhong-Hai Ren et al., "," Nature Genetics, vol. 37, No. 10, pp. 1141-1146 (Oct. 2005).
Sequence Accession AQD44779, as cited at pp. 5-6 in the Office action of Aug. 26, 2019 issued in U.S. Appl. No. 15/798,384, filed Jun. 12, 2008.

\* cited by examiner

SEQUENCE LISTING

```
<160> NUMBER OF SEQ ID NOS: 13

<210> SEQ ID NO 1
<211> LENGTH: 1835
<212> TYPE: DNA
<213> ORGANISM: Oryza sativa

<400> SEQUENCE: 1
acttgtacta cctcattggc acaggcacat tcttgtggga gaaattttgg atagagaaat        60
ggagatgatg ctcctgatgc tgggaaagaa catcacatgc ttgcatgctc ctcgacgtga       120
tgagcaacat gtaagtatat gttagtactg cagtagtgcc cttgcagcat cgatcaccaa       180
ccaatctgtc gcctgcatgg cagaatctga ttgtctgttc ctcacaaaca tgtcatattc       240
tgatgcctcc tagcaatctg aattactacc atattaaaat tttcacccct cctgatggtg       300
```

```
ttttcacctt ctgttctgac acatatgtta agatttcaag ttgttcaggg aaacacttgt      360
gatatgtata tccacccatc ccaccagggt tcaagtcctg ttgcccatga atattacaga      420
catactagtg ggcattcaat agaatttagt aagatcaggg atgtgttgtg gattcccgtc      480
tctttgagca tgtgttagat ggcgcatctg tcattgtgtg agtgtggtgt tacgtgtgta      540
gtgttgtgca tgcatttaca tctgtcgtgt aatcgcaaaa agatttcagg ttgttcaggt      600
gtgtatgtgt tcagtgtatc tctgaattga tctgtgctgt tgctgcatat gctgaagctg      660
acacacatat gttcagtttc agagttcagt ctgtttcgag tgttcaatgt atctctgaac      720
tgatcactgt tgatgctgaa tatactacgc tgaagacgac actgacattt tgactaactg      780
ggtgcctata atcagcacgg aatacacgag gaaaaacaaa aaatgaagcg ccactaatca      840
gttaattacc gtttcaaatg atccatcatt agccaataca tgcatgaatt tttcgtgcgg      900
aatgcccact gctagaactg cgaaacaccc taattctcgc tgaatttgtg tgcatgtata      960
tccatccatt catcgttcgg ctgcctaaca gctggaaaaa tgactttgtg catcttgtga     1020
gaattgcagc taaagtcagg ttagctctga aagtgctcta ccctgcattc ttgccaaggt     1080
taaattcttc caaccaatac acgctctcga atcgaacctt atcactcttg tcataaatta     1140
agctgcaaga atcagatgat tccacagttc agataaccct caagaaaaga acttcacaag     1200
ttcagaattc agactgactt aattcaccag gttgccgaaa attcactgca agtactaatg     1260
cagtgcagcc gtacgaacct atctgtacgg tcgatacgaa tttaagcaaa aatccgatcc     1320
atcattataa tctaaatttg agagtctgat caaacccaga tttaaactaa ttttaccag     1380 gttgctcaaa attcactgca cgtactagtg cagtgcagcc gacaaatcca tctgtacagt     1440
tgatacgaat ttaaagcaaa attaaatcca tctttataat ctaaatttga gaatctgatc     1500
aaacccagac ttaaactaat ttttacctgc ttgctcaaaa ttcactgcaa ggactagtgc     1560
agtgcagccg acaaatacat ctgtacagtt aatgaaattt taaagcgaaa ttcaatttaa     1620
attcgagaga gagaagaaga agaagaagaa gaaagacaga ctaatcatgc caacttgcaa     1680
gcccaaagac ccaatctttc cttagaaatt taattttttt ttcatctctt tcctcgcgtt     1740
ttccctccct ttataaccac caccaccatc tcgtctcctt cctcccgctc gcttactgct     1800
cgactcgtcg ccttcctcct cgtggcgagc gatcg                               1835
```

<210> SEQ ID NO 2
<211> LENGTH: 639
<212> TYPE: DNA
<213> ORGANISM: Oryza sativa
<220> FEATURE:
<221> NAME/KEY: CDS
<222> LOCATION: (1)..(636)

<400> SEQUENCE: 2

```
atg agg acg ggg gag gtg gcg gag gcg gtg ccg agg gtg gtg gcg atc        48
Met Arg Thr Gly Glu Val Ala Glu Ala Val Pro Arg Val Val Ala Ile
1               5                   10                  15 ctg tcg tcg ctg ctg cag cgg gtg gcg gag cgg aac gac gcg gcg gcg        96
Leu Ser Ser Leu Leu Gln Arg Val Ala Glu Arg Asn Asp Ala Ala Ala
            20                  25                  30 gcg gcg gcg gcg gtg ggg gag gag gcg gcg gcg gtg tcg gcg ttc cag       144
Ala Ala Ala Ala Val Gly Glu Glu Ala Ala Ala Val Ser Ala Phe Gln
        35                  40                  45 ggg ctg acg aag ccg gcg ata tcc atc gga ggg tac ctg gag cgg atc       192
Gly Leu Thr Lys Pro Ala Ile Ser Ile Gly Gly Tyr Leu Glu Arg Ile
    50                  55                  60
```

```
ttc cgg ttc gcc aac tgc agc ccg tcg tgc tac gtc gcc tac atc      240
Phe Arg Phe Ala Asn Cys Ser Pro Ser Cys Tyr Val Ala Tyr Ile
 65                  70                  75                  80 tac ctc gac cgc ttc ctc cgc cgc cct gcc ctc gcc gtc gac tcc      288
Tyr Leu Asp Arg Phe Leu Arg Arg Pro Ala Leu Ala Val Asp Ser
                 85                  90                  95 ttc aac gtc cac cgc ctc ctc atc aca tcc gtc ctc acc gcc gtc aag  336
Phe Asn Val His Arg Leu Leu Ile Thr Ser Val Leu Thr Ala Val Lys
            100                 105                 110 ttc gtc gac gac ata tgc tac aac aat gcc tac ttc gcg agg gtg gga  384
Phe Val Asp Asp Ile Cys Tyr Asn Asn Ala Tyr Phe Ala Arg Val Gly
        115                 120                 125 ggc atc agc ttg atg gag atg aat tat ctt gag gtg gac ttc ctc ttt  432
Gly Ile Ser Leu Met Glu Met Asn Tyr Leu Glu Val Asp Phe Leu Phe
    130                 135                 140 ggc atc gcc ttc gac ctc aat gtc acg ccg gct gcc ttc gcc tcc tac  480
Gly Ile Ala Phe Asp Leu Asn Val Thr Pro Ala Ala Phe Ala Ser Tyr
145                 150                 155                 160 tgc gcc gtg ctg cag agc gag atg acc tac ctg gag cag ccg ccc gcc  528
Cys Ala Val Leu Gln Ser Glu Met Thr Tyr Leu Glu Gln Pro Pro Ala
                165                 170                 175 gtc gat ctc ccc agg ctg cac tgc tgt ccg tcc gat cag gac gat gcc  576
Val Asp Leu Pro Arg Leu His Cys Cys Pro Ser Asp Gln Asp Asp Ala
            180                 185                 190 ggc tgc cat cac aag cag cag cag cag cag caa caa cag cag cag cat  624
Gly Cys His His Lys Gln Gln Gln Gln Gln Gln Gln Gln Gln Gln His
        195                 200                 205 cag ctc gcc gtc tga                                              639
Gln Leu Ala Val
    210

<210> SEQ ID NO 3
<211> LENGTH: 212
<212> TYPE: PRT
<213> ORGANISM: Oryza sativa

<400> SEQUENCE: 3

Met Arg Thr Gly Glu Val Ala Glu Ala Val Pro Arg Val Val Ala Ile
 1               5                  10                  15

Leu Ser Ser Leu Leu Gln Arg Val Ala Glu Arg Asn Asp Ala Ala
            20                  25                  30

Ala Ala Ala Ala Val Gly Glu Glu Ala Ala Val Ser Ala Phe Gln
        35                  40                  45

Gly Leu Thr Lys Pro Ala Ile Ser Ile Gly Gly Tyr Leu Glu Arg Ile
    50                  55                  60

Phe Arg Phe Ala Asn Cys Ser Pro Ser Cys Tyr Val Ala Tyr Ile
65                  70                  75                  80

Tyr Leu Asp Arg Phe Leu Arg Arg Pro Ala Leu Ala Val Asp Ser
                85                  90                  95

Phe Asn Val His Arg Leu Leu Ile Thr Ser Val Leu Thr Ala Val Lys
            100                 105                 110

Phe Val Asp Asp Ile Cys Tyr Asn Asn Ala Tyr Phe Ala Arg Val Gly
        115                 120                 125

Gly Ile Ser Leu Met Glu Met Asn Tyr Leu Glu Val Asp Phe Leu Phe
    130                 135                 140

Gly Ile Ala Phe Asp Leu Asn Val Thr Pro Ala Ala Phe Ala Ser Tyr
145                 150                 155                 160
```

```
Cys Ala Val Leu Gln Ser Glu Met Thr Tyr Leu Glu Gln Pro Pro Ala
                165                 170                 175

Val Asp Leu Pro Arg Leu His Cys Cys Pro Ser Asp Gln Asp Asp Ala
            180                 185                 190

Gly Cys His His Lys Gln Gln Gln Gln Gln Gln Gln Gln Gln Gln His
        195                 200                 205

Gln Leu Ala Val
    210

<210> SEQ ID NO 4
<211> LENGTH: 212
<212> TYPE: PRT
<213> ORGANISM: Oryza sativa

<400> SEQUENCE: 4

Met Arg Thr Gly Glu Val Ala Glu Ala Val Pro Arg Val Val Ala Ile
1               5                   10                  15

Leu Ser Ser Leu Leu Gln Arg Val Ala Glu Arg Asn Asp Ala Ala Ala
            20                  25                  30

Ala Ala Ala Val Gly Glu Glu Ala Ala Val Ser Ala Phe Gln
        35                  40                  45

Gly Leu Thr Lys Pro Ala Ile Ser Ile Gly Gly Tyr Leu Glu Arg Ile
    50                  55                  60

Phe Arg Phe Ala Asn Cys Ser Pro Ser Cys Tyr Val Ala Tyr Ile
65                  70                  75                  80

Tyr Leu Asp Arg Phe Leu Arg Arg Pro Ala Leu Ala Val Asp Ser
                85                  90                  95

Phe Asn Val His Arg Leu Leu Ile Thr Ser Val Leu Thr Ala Val Lys
            100                 105                 110

Phe Val Asp Asp Ile Cys Tyr Asn Asn Ala Tyr Phe Ala Arg Val Gly
            115                 120                 125

Gly Ile Ser Leu Met Glu Met Asn Tyr Leu Glu Val Asp Phe Leu Phe
        130                 135                 140

Gly Ile Ala Phe Asp Leu Asn Val Thr Pro Ala Ala Phe Ala Ser Tyr
145                 150                 155                 160

Cys Ala Val Leu Gln Ser Glu Met Thr Tyr Leu Glu Gln Pro Pro Ala
                165                 170                 175

Val Asp Leu Pro Arg Leu His Cys Cys Pro Ser Asp Gln Asp Asp Ala
            180                 185                 190

Gly Cys His His Lys Gln Gln Gln Gln Gln Gln Gln Gln Gln Gln His
        195                 200                 205

Gln Leu Ala Val
    210

<210> SEQ ID NO 5
<211> LENGTH: 40
<212> TYPE: DNA
<213> ORGANISM: Artificial Sequence
<220> FEATURE:
<223> OTHER INFORMATION: DNA Primer
<220> FEATURE:
<221> NAME/KEY: primer_bind
<222> LOCATION: (1)..(40)
<223> OTHER INFORMATION: Primer CYCU4-U

<400> SEQUENCE: 5
atatgagctc atgaggacgg gggaggtggc ggaggcggtg                          40
```

```
<210> SEQ ID NO 6
<211> LENGTH: 37
<212> TYPE: DNA
<213> ORGANISM: Artificial Sequence
<220> FEATURE:
<223> OTHER INFORMATION: DNA Primer
<220> FEATURE:
<221> NAME/KEY: primer_bind
<222> LOCATION: (1)..(37)
<223> OTHER INFORMATION: primer CYCU4-L-1

<400> SEQUENCE: 6
cgtctttgta gtcgacggcg agctgatgct gctgctg                              37

<210> SEQ ID NO 7
<211> LENGTH: 46
<212> TYPE: DNA
<213> ORGANISM: Artificial Sequence
<220> FEATURE:
<223> OTHER INFORMATION: DNA Primer
<220> FEATURE:
<221> NAME/KEY: primer_bind
<222> LOCATION: (1)..(46)
<223> OTHER INFORMATION: Primer CYCU4-L-2

<400> SEQUENCE: 7
atattctaga ctacttgtcg tcatcgtctt tgtagtcgac ggcgag                    46

<210> SEQ ID NO 8
<211> LENGTH: 20
<212> TYPE: DNA
<213> ORGANISM: Artificial Sequence
<220> FEATURE:
<223> OTHER INFORMATION: DNA Primer
<220> FEATURE:
<221> NAME/KEY: primer_bind
<222> LOCATION: (1)..(20)
<220> FEATURE:
<221> NAME/KEY: primer_bind
<222> LOCATION: (1)..(20)
<223> OTHER INFORMATION: primer CYCU4; 1: R-

<400> SEQUENCE: 8
tgaggtggac ttcctctttg                                                 20

<210> SEQ ID NO 9
<211> LENGTH: 20
<212> TYPE: DNA
<213> ORGANISM: Artificial Sequence
<220> FEATURE:
<223> OTHER INFORMATION: DNA Primer
<220> FEATURE:
<221> NAME/KEY: primer_bind
<222> LOCATION: (1)..(20)
<223> OTHER INFORMATION: primer CYCU4;1: F-

<400> SEQUENCE: 9
ccaggtaggt catctcgctc                                                 20

<210> SEQ ID NO 10
<211> LENGTH: 38
<212> TYPE: DNA
<213> ORGANISM: Artificial Sequence
<220> FEATURE:
<223> OTHER INFORMATION: DNA Primer
<220> FEATURE:
<221> NAME/KEY: primer_bind
<222> LOCATION: (1)..(38)
<223> OTHER INFORMATION: primer pCYCU4-U

<400> SEQUENCE: 10
```

```
atataagctt acttgtacta cctcattggc acaggcac                                    38

<210> SEQ ID NO 11
<211> LENGTH: 35
<212> TYPE: DNA
<213> ORGANISM: Artificial Sequence
<220> FEATURE:
<223> OTHER INFORMATION: DNA Primer
<220> FEATURE:
<221> NAME/KEY: primer_bind
<222> LOCATION: (1)..(35)
<223> OTHER INFORMATION: primer pCYCU4-L

<400> SEQUENCE: 11
atatggatcc cgatcgctcg ccacgaggag gaagg                                       35

<210> SEQ ID NO 12
<211> LENGTH: 18
<212> TYPE: DNA
<213> ORGANISM: Artificial Sequence
<220> FEATURE:
<223> OTHER INFORMATION: DNA Primer
<220> FEATURE:
<221> NAME/KEY: primer_bind
<222> LOCATION: (1)..(18)
<223> OTHER INFORMATION: primer RNAi- CYCU4;1: R-

<400> SEQUENCE: 12
gtcgcctaca tctacctc                                                          18

<210> SEQ ID NO 13
<211> LENGTH: 21
<212> TYPE: DNA
<213> ORGANISM: Artificial Sequence
<220> FEATURE:
<223> OTHER INFORMATION: DNA Primer
<220> FEATURE:
<221> NAME/KEY: primer_bind
<222> LOCATION: (1)..(21)
<223> OTHER INFORMATION: primer RNAi- CYCU4;1: F-

<400> SEQUENCE: 13
gataattcat ctccatcaag c                                                      21
```

GENE FOR CONTROLLING ERECTNESS GROWTH OF RICE LEAF BLADES AND APPLICATION THEREOF

CROSS-REFERENCE TO RELATED APPLICATIONS

The subject application is a continuation of U.S. patent application Ser. No. 15/798,384 filed on Oct. 30, 2017, which in turn is a continuation of PCT/CN2016/080098 filed on Apr. 23, 2016 and claims priority on Chinese application no. 201510219253.2 filed on Apr. 29, 2015. The contents and subject matter of all the priority applications are incorporated herein by reference.

TECHNICAL FIELD

The present invention relates to plant genetic engineering, particularly, a gene and a vector containing the gene or a homologous gene thereof and the application for regulating leaf erectness of plants in agricultural production.

BACKGROUND OF INVENTION

The architecture of crops is a key characteristic for high-yield breeding. Leaf erectness (or the leaf-stem angle) is one of the important characteristics for plant architecture development. The field planting density of crops may be increased with a proper leaf-stem angle to further promote the utilization ratio of light energy and increase the yield of crops. The leaf pulvinus plays a key role in leaf erectness, and its development directly affects the leaf erectness. Therefore, finding and utilizing the key gene affecting the leaf erectness (or the leaf-stem angle) is the key to improve the rice architecture for promoting the breeding via molecular design and increasing the rice yield per unit area.

The leaf pulvinus of monocotyledonous plants is an intermediate hub connecting the leaf blade and leaf sheath and serves as a basic structure for forming the leaf-stem angle. As a mechanical mechanism, the leaf pulvinus promotes the leaf blade to bend towards an abaxial direction when the leaf blade and the leaf sheath undergo complete elongation, therefore, the development of leaf pulvinus closely relates to the leaf erectness. Both brassinosteroids (BR) synthesis and signaling pathways play an important and unique role in regulating the leaf erectness in monocotyledons, however, the underlying cytology and molecular mechanisms are unknown. It is reported that mutants in BR synthesis pathway, d2, dwarf4, d11, and brd2, are all characterized by erect leaves. A positive-regulator-deficient mutant in the BR signaling pathway is also characterized by a small leaf-stem angle and erecting leaf, such as receptor mutants d61, dlt, d1, and tud1. The transgenic plants of OsBAK1 and OsGSK2, which are obtained by homologous cloning, exhibit changes in the leaf-stem angle. The leaf erectness may also be promoted by suppressing the gene expression of the positive regulator OsBZR1 at the downstream of the rice BR signaling pathway via RNAi technology. Moreover, a gain-of-function mutant lic-1, a negative regulator of the BR signaling pathway, is also characterized by a small leaf-stem angle and erecting leaf. A gain-of-function mutant ili1-D is characterized by a large leaf-stem angle due to the amplification of a BR signal. In addition, a target gene OsIBH1 of OsBZR1 is directly involved in the leaf erectness regulation in rice; and the external application of BR enlarged leaf angles of wild type and BR-synthesis mutants, and the BR signaling mutant, such as a receptor mutant d61, is almost unaffected.

In addition to the brassinosteroids pathways, other signaling pathways are also involved in the regulation of the leaf-stem angle. Although the genes of the BR-related pathways play a significant role in regulating the rice leaf angles, other independent pathways are also involved in the regulation of such biological characters. When decreasing the expression level of SPINDLY (SPY), a negative regulated gibberellin signal, the leaf-stem angle can be increased. However, the leaf-stem angle of the rice may be increased due to the over-expression of a family member OsIAA1, a negative regulator in auxin signaling pathway. LC1, encoding a gene for regulating the auxin homeostasis, determines the rice leaf-stem angle by regulating the cell elongation in the leaf pulvinus. Rice leaf inclination2 (LC2), a VIN3-analogous protein, may also enlarge the leaf-stem angle after mutation. A gene ILA1, a member in Group C of a MAPKKK family, has a high expression in a vascular bundle of the leaf pulvinus, and the insertional mutation of ILA1 thereof leads to the decrease of the contents of major components including fibrin and xylan in the cell wall of the leaf pulvinus, resulting in the reduction of the mechanical strength of the leaf pulvinus and the increase of the leaf angle. A mutant of LPA1, a Loose Plant Architecture1 in the rice, is characterized as a loose architecture with both the tiller angle and leaf-stem angle increased.

Leaf erectness has been demonstrated to be closely related with the crop yields. There is a broad application prospect in the crop yields by using the gene in the BR-related pathway as a target gene for improving the rice architecture. For example, the expression of endogenous OsBRI1 of the rice is partially suppressed by introducing an intracellular region (OsACTIN::OsBRI1-KD) of OsBRI1 as driven by a rice actin promoter with a co-suppression strategy, thereby an erect leaf transgenic line is isolated from the offspring; and the yield is estimated to increase by about 35% and 26% through close planting. Through field experiments, it has been demonstrated that the yield may be increased by up to 32% by the reasonable close planting of the mutant based on a BR synthesis pathway OsDWARF4 of the rice. 244 RIL groups from Zhenshan 97B and Miyan 46 are genetically analyzed in terms of the flag leaf angle and the main ear output. Five QTLs for controlling the flag leaf angle have been detected in total on chromosomes 1, 3, 5 and 11, where the QTL for controlling the flag leaf angle (FLA) and seed setting percentage (SF) have been detected simultaneously at an interval RM24-RM294A of the chromosome 1, with opposite additive effect directions. It demonstrates that the flag leaf angle is in negative correlation with the yield, and it is favorable to increase the seed settling percentage by properly reducing the flag leaf angle of the rice, and to finally increase the yield.

SUMMARY OF THE INVENTION

The present invention provides a gene for controlling rice leaf erectness development, in which with a reverse genetics method, a gene, specifically expressing in a leaf pulvinus, is screened through the specific gene expression chip analysis of a rice leaf and pulvinus, and the promoter of CYC U4;1 is proved to have a specific expression in the sclerenchyma cell of leaf pulvinus by utilizing a pCYCU4-GUS transgenic line and in situ hybridization; and by transgenically increasing the expression level of CYC U4;1 and decreasing the expression level of CYC U4;1 with RNAi technology, the gene CYC U4;1 is proved to be capable of controlling the rice leaf erectness development. The present invention provides a vector containing the gene or a homologous gene thereof and an application involving regulating the leaf erectness of plants by utilizing the gene or a functional analog thereof in agricultural production.

One object of the present invention is to provide a gene CYC U4;1 for controlling the leaf erectness in rice. The gene is identified from a specific expression chip of a rice leaf pulvinus and is isolated and cloned. The promoter region of CYC U4;1 as shown in SEQ ID NO: 1, the CDS nucleotide sequence of CYC U4;1 as shown in SEQ ID NO: 2 and the amino acid sequence of CYC U4;1 as shown in SEQ ID NO: 3.

Another object of the present invention is to provide an application of the gene CYC U4;1 to controlling of the rice leaf erectness. A leaf-stem angle may be reduced by overexpression of the CYC U4;1 driven by the native promoter (with the sequence as shown in SEQ ID NO: 1) of the gene CYC U4;1, thereby improving the architecture of rice varieties and increasing the plant density per unit area.

To achieve the objects as described above, a technical solution employed by the present invention is as follows.

Using a gene specific expression chip assay in rice leaf blades and pulvini the inventor created, a gene CYC U4;1 with a specific expression at the leaf pulvinus is selected from differentially expressed genes of the chip with a reverse genetics method, and the specific expression of CYC U4;1 at the leaf pulvinus is verified with real-time qRT-PCR. A gene CYC U4;1 for controlling erectness development of rice leaves is obtained with the following method.

The total volume of a reaction system is 50 µl, with a template including Nipponbare cDNA 1 ul (about 50 ng), 10×KOD enzyme reaction buffer (5 µl), 25 mM $MgCL_2$ (2 µl), 5 mM dNTP (5 µl), 5 uM primers (5 µl) (with a stepwise PCR means, primers CYCU4-U having SEQ ID NO: 4 and CYCU4-L-1 having SEQ ID NO: 5 are used the first time, and primers CYCU4-U having SEQ ID NO: 4 and CYCU4-L-2 having SEQ ID NO: 6 are used the second time, with each primer at 2.50), KOD enzyme (1 µl), and the balance of $ddH_2O$ (sterile deionized water) which is added till the total volume of 50 µl.

A reaction procedure is as follows: denaturing at 94° C. for 5 min, 94° C. for 30 sec, 55° C. for 1 min and 68° C. for 2 min for 35 cycles in total, and elongating at 68° C. for 10 min The primers are described as follows:

```
CYCU4-U:
                                          (SEQ ID NO: 4)
ATATgagctcATGAGGACGGGGGAGGTGGCGGAGGCGGTG;

CYCU4-L-1:
                                          (SEQ ID NO: 5)
CGTCTTTGTAGTCGACGGCGAGCTGATGCTGCTGCTG;
and CYCU4-L-2:
                                          (SEQ ID NO: 6)
ATATtctagactaCTTGTCGTCATCGTCTTTGTAGTCGACGGCGAG.
```

A gene sequence containing the nucleotide as described in SEQ ID NO: 2 is finally obtained, and a protein sequence encoded by the gene is as shown in SEQ ID NO: 3.

The present invention also provides the promoter region (with the sequence as shown in SEQ ID NO: 1) of the gene CYC U4;1, a nucleotide sequence (with the sequence as shown in SEQ ID NO: 2) corresponding to an amino acid sequence as shown in SEQ ID NO: 3, as well as a protein having the same function, which is obtained by modifying the sequence as shown in SEQ ID NO: 3.

An application of the gene CYC U4;1 to controlling the erectness of the rice leaves comprises cloning a promoter and full-length CDS of CYC U4;1 to pCAMBIA1301 and transferring it into the Nipponbare, and transgenic lines obtained are characterized by having a smaller leaf-stem angle than those of wild rice (Nipponbare), therefore, the leaf-stem angle may be reduced with this method to increase the planting density.

Compared with the prior art, the present invention has the following advantages:

1. CYC U4;1 is a gene having a specific expression only in the leaf pulvinus of rice in a seedling stage, which makes it possible to only change the leaf-stem angle of the crops by using the gene without affecting other characters.

2. As an effective gene for changing the leaf-stem angle, CYC U4;1 may directly affect the specific cell division at the leaf pulvinus to further change the leaf-stem angle of the crops;

3. At present, the molecular mechanism of the leaf erectness regulated by brassinosteroids to further increase the yield of crops is still not clear, and the gene uncovered the cellular and molecular mechanism that brassinosteroids regulated the erectness of the leaves.

BRIEF DESCRIPTION OF THE DRAWINGS

FIGS. 2A and 2B show the GUS staining results of pCYCU4::GUS transgenic rice, in which FIG. 2A shows the phenotype of the transgenic rice plant, and FIG. 2B shows the microscopic cross-sectional view of the GUS staining in the transgenic rice plant, with the arrow indicating the expression of CYC U4;1 in the leaf pulvinus.

FIGS. 5A and 5B show and compare the phenotype and expression level of a plurality of independent pCYCU4::CYC U4;1 and RNAi-CYC U4;1 transgenic lines, in which, FIG. 5A shows multiple plants in the RNAi-CYC U4;1 transgenic lines having wide leaf-stem angle, and FIG. 5B shows multiple plants in the pCYCU4::CYCU4;1 transgenic lines having narrow leaf-stem angle.

DETAILED DESCRIPTION OF THE INVENTION

The present invention is further illustrated in the following embodiments.

Embodiment 1

A gene CYC U4;1 for controlling erectness development of rice leaves is obtained by using a gene specific expression chip in leaf blades and pulvini created by the inventors, and a gene CYC U4;1 with a specific expression at the leaf pulvinus is selected from differentially expressed genes of the chip with a reverse genetics method, and the specific expression of CYC U4;1 at the leaf pulvinus is verified with real-time qRT-PCR.

The details are as follows. A gene CYC U4;1 for controlling erectness development of rice leaves is obtained with the following method. The total volume of a reaction system is 50 μl, with a template including Nipponbare CDNA 1 ul (about 50 ng), 10×KOD enzyme reaction buffer (5 μl), 25 mM MgCL$_2$ (2 μl), 5 mM dNTP (5 μl), 5 uM primers (5 μl) (with a stepwise PCR means, primers CYCU4-U having SEQ ID NO: 4 and CYCU4-L-1 having SEQ ID NO: 5 are used the first time, and primers CYCU4-U having SEQ ID NO: 4 and CYCU4-L-2 having SEQ ID NO: 6 are used the second time, with each primer at 2.5 μl), KOD enzyme (1 μl) and the balance of ddH$_2$O (sterile deionized water) which is added to the total volume of 50 μl.

The reaction procedure is as follows: denaturing at 94° C. for 5 min, 94° C. for 30 sec, 55° C. for 1 min and 68° C. for 2 min for 35 cycles in total, and elongating at 68° C. for 10 min.

The primers used are as follows:

```
CYCU4-U:
                                                (SEQ ID NO: 4)
ATATgagctcATGAGGACGGGGGAGGTGGCGGAGGCGGTG;

CYCU4-L-1:
                                                (SEQ ID NO: 5)
CGTCTTTGTAGTCGACGGCGAGCTGATGCTGCTGCTG;

CYCU4-L-2:
                                                (SEQ ID NO: 6)
ATATtctagactaCTTGTCGTCATCGTCTTTGTAGTCGACGGCGAG.
```

A sequence of the gene CYC U4;1 containing the nucleotide as described in SEQ ID NO: 2 is finally obtained, and an amino acid sequence encoded with the gene is as shown in SEQ ID NO: 3.

Figure 1:
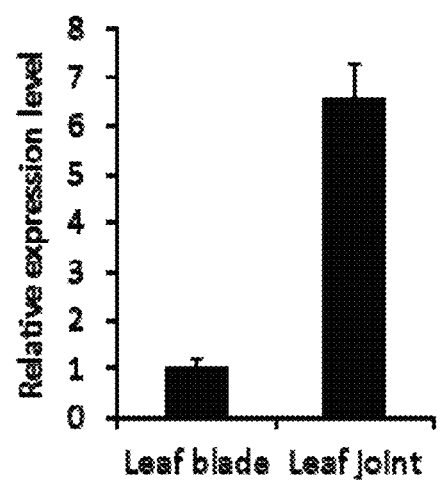
FIG. 1 shows verification of specific expression of CYC U4;1 in a rice pulvinus by Realtime qRT-PCT.

Real time qRT-PCT is used to verify the specific expression of CYC U4;1 in a rice pulvinus as follows: A leaf blade and a leaf pulvinus are taken from the rice seedling of Nipponbare growing for one week, the total RNA is extracted with a TiangenRNApre Plant Kit (Tiangen), then a first-chain cDNA is synthesized with a Takara PrimeScript First-strand cDNA synthesis kit (TaKaRa), and the relative expression level of CYCY U4;1 in the leaf blade and leaf pulvinus is detected by the real-time quantitative PCR. The primers for the real-time quantitative PCR are as follows: CYCU4;1: R-TGAGGTGGACTTCCTCTTTG (SEQ ID NO: 7); F-CCAGGTAGGTCATCTCGCTC (SEQ ID NO: 8). It is found that the gene CYC U4;1 has a specific expression at the leaf pulvinus as shown in FIG. 1.

Embodiment 2

The application of the gene CYC U4;1 to controlling of the erectness of the rice leaves is performed in a process as follows:

1) Building of Plant Expression Vector pCYCU4;1-GUS

A promoter region of CYC U4;1 is amplified, and a fragment is cloned to a pCAMBIA1300GN GUS vector (Ren Z H, Gao J P, Li L G, et al. A rice level quantitative trait locus for salt tolerance encodes a sodium transporter [J]. Nature genetics, 2005, 37(10): 1141-1146) by using a HindIII/BamH1 enzyme digestion site.

The promoter region of CYC U4;1 is obtained by means of the following.

The total volume of a reaction system is 50 μl, with a template including a Nipponbare genome DNA 1 ul (about 50 ng), 1×KOD enzyme reaction buffer (5 μl), 25 mM MgCL$_2$ (2 μl), 5 mM dNTP (5 μl), 5 uM primers (5 μl) (primers pCYCU4-U having SEQ ID NO: 9 and pCYCU4-L having SEQ ID NO: 10, each of 2.5 μl), KOD enzyme (1 μl) and the balance of ddH$_2$O (sterile deionized water) which is added to the total volume of 50 μl. The reaction procedure is as follows: denaturing at 94° C. for 5 min, 94° C. for 30 sec, 55° C. for 1 min and 68° C. for 2 min for 35 cycles in total, and elongating at 68° C. for 10 min.

The primers used are as follows:

```
pCYCU4-U:
                                                (SEQ ID NO: 9)
atatAAGCTTacttgtactacctcattggcacaggcac;

pCYCU4-L:
                                                (SEQ ID NO: 10)
atatGGATCCcgatcgctcgccacgaggaggaagg.
```

The promoter region of the gene CYC U4;1 as shown in SEQ ID NO: 1 is finally obtained.

2) Building of Plant Expression Vector pCYCU4::CYC U4;1

The promoter region of CYC U4;1 is amplified with a stepwise method (a method for amplifying the promoter region is the same as Step 1)), a fragment is cloned to pCAMBIA1301 by using a HindIII/BamH1 enzyme digestion site to obtain pCAMBIA1301-pCYCU4;1, then a full-length cDNA (as shown in SEQ ID NO: 2) of CYC U4;1 connected with a FLAG label is cloned to pCAMBIA1301-pCYCU4;1 by using Sac1/Xba1 to obtain a plant expression vector pCYCU4::CYC U4;1, which is transferred into the Nipponbare.

3) Building of Plant Expression Vector RNAi-CYC U4;1

CYC U4;1 (345-639 bp) is cloned to an RNAi vector pTCK303 by using Kpn1/BamH1 and Sac1/Spe1 enzyme digestion sites and then transferred into the Nipponbare.

4) Genetic Transformation of Rice

In Steps 1) to 3), the transformation of the rice is performed with a genetic transformation method mediated with *agrobacterium* EHA105, with the details as follows:

① Callus induction. Rice seeds are shelled, and clear saturated grains are soaked in 70% ethanol for 1 min at first and rinsed 1 to 2 times with sterile water; and then, the grains are soaked in an NaClO solution containing 2% active chlorine (in case of 40 ml of NaClO solution containing the active chlorine of more than 5.2%, 60 ml water is added) added with 1 to 3 drops of Tween 20, for 30 min (generally 40 min, and 1 h at the most). Shaking is performed from time to time and then sterile water is used for rinsing 4 to 5 times. The grains are poured onto a sterilized flat plate and dried with filter paper for about 1 hour. The grains are placed into an N6D solid culture medium (10 grains/25 ml/bottle), with seed embryos facing upwards or in contact with the culture medium, and cultured in darkness at 28° C. for 25 to 30d. The N6D2 culture medium includes N6 salts and vitamins, 0.5 g/l of casein hydrolysate, 30 g/l of cane sugar, 2 mg/l of 2,4-D, and 2.5 g/l of Phytagel (Sigma), at pH5.8.

② Culture of agrobacteria and co-culture of rice calluses. A sterilized spoon is used to obtain the agrobacteria by scraping, and the *agrobacterium* is slightly tapped to a loose state against a tube wall with a spoon back, with OD600=0.8-1.0. The pre-cultured calluses are aired on the sterile filter paper and then centralized in a vessel and transferred into an agrobacteria solution in one step, a centrifugal tube is slightly rotated to uniformly distribute the agrobacterial solution, and standing is performed for about 15 to 20 min. The agrobacteria solution is poured out, the calluses are placed on the sterile filter paper for 1.5h to ensure that the agrobacteria solution is completely absorbed, then transferred into ½ N6D AS and cultured in darkness at 20° C. for 2-3 days, and the agrobacteria can be removed when a bacterial film appears at a place where the calluses are in contact with the culture medium. A ½ N6D AS culture medium includes N6D2, 10 g/l of glucose, and 100-400 μmol/l of acetosyringone (added on the spot when in use), at pH5.2.

③ Removal of agrobacteria. The calluses subjected to co-culture are added into a 50 ml centrifugal tube and cleaned more than 3 times with sterile water until the liquid is clear. The sterile water is poured out, and the calluses are cultured with N6D+Cn (500 mg/L) (or AP500 ml/L) at 100 rpm for 15-20 min for 2 to 3 times. The calluses are placed on the sterile filter paper and dried for about 2h as appropriate. The dried calluses are transferred into N6D-AS and cultured in darkness at 28° C. for 7 to 10d with the addition of cephalosporin Cn (250 mg/L).

④ Screening of calluses. The calluses which are not contaminated by the agrobacteria are picked out, and combined with Cn250 mg/L and Hn (50 mg/L) during the first time for screening for 15 to 20d. For the second time, the operation is the same as above except for that Cn is not added, instead hygromycin (Hn) is added, and all the calluses are transferred again completely for 15 to 20d. For the third time, the new calluses are chosen out and screened with Hn for 15 to 20d. It is not necessary to arrange the order as above, however, the screening time for the calluses on the Hn shall be ensured to be at least above 45d, and it would be best to screen the newly grown calluses picked out for the third time for 20d. An N6D screening culture medium includes N6D+Cn (250 mg/L)+Hn (50 mg/L) at PH=5.8-5.9.

⑤ Differentiation and rooting. All the calluses screened the fourth time are transferred into MS and cultured in darkness with Hn (50 mg/L) for pre-differentiation (at PH 5.9) for 12 to 15d. Fresh well-growing calluses are chosen and transferred into MS (PH 6.0) for light culture for 15 to 20d. Green buds can be seen growing, and the culture medium is generally changed every 15d. The green buds growing to more than 1 cm are chosen, with surplus surrounding calluses stripped and the roots cut-off (with about 0.5 cm left), and are transferred into a test tube for rooting culture in ½ MS. An MS differentiation culture medium includes MS salts and vitamins, 2 g/l of casein hydrolyzate, 30 g/l of cane sugar, 25 g/L of sorbitol, 2 mg/l of 6-BA, 0.5 mg/l of NAA, 0.2 mg/l of Zeatin, 0.5 mg/l of KT, 3.0 g/l of Phytagel (pH 5.8), 50 mg/l of hygromycin B, and 200 mg/l of cephalosporin; and a ½ MS rooting culture medium includes ½MS salts, MS vitamins, 30 g/l of cane sugar, 1 mg/l of paclobutrazol, 0.5 mg/l of NAA, 50 mg/l of hygromycin, and 2.5 g/l of Phytagel, at pH 5.8.

5) Transplanting, identification of expression level and phenotype analysis. 40 lines are genetically built from each of the rooting transgenic plants and transplanted in a greenhouse, and leaf blades are taken to undergo expression level identification based on real-time qRT-PCR and GUS staining analysis. RNAi-CYCU4;1: R-GTCGCCTACATC-TACCTC (having SEQ ID NO: 11); F-GATAATTCATCTC-CATCAAGC (having SEQ ID NO: 12).

Figures 2A, 2B:
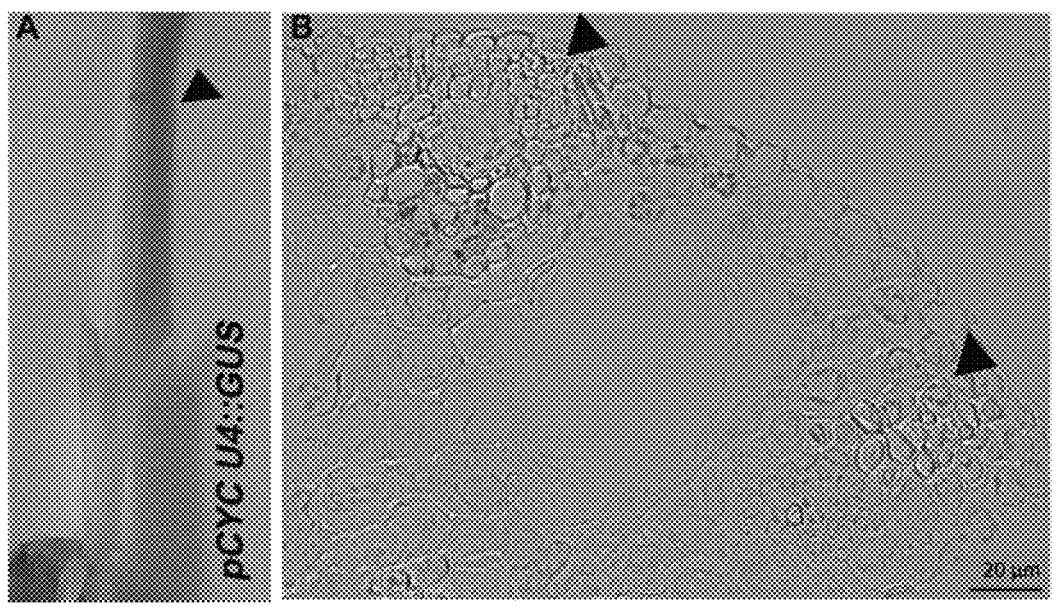

6) Results:

(1) By transferring the obtained vector into the rice Nipponbare and with a pCYCU4;1::GUS transgenic rice report system, it is indicated that CYC U4;1 is mainly expressed in the leaf pulvinus as shown in FIGS. 2A and 2B.

Figure 3A:
FIGS. 3A and 3B show phenotypes and transgenic expression levels of pCYCU4::CYC U4;1 transgenic rice (marked as CYC U4;1) in comparison to the wild type rice (marked as Ni for Nipponbare), in which, FIG. 3A compares the phenotype and transgenic expression level of the wild type rice (Ni) and transgenic rice (CYC U4;1) in a maturation stage, and FIG. 3B compares the phenotype and transgenic expression level of the wild type rice (Ni) and transgenic rice (CYC U4;1) in a seedling stage.
Figure 3B:
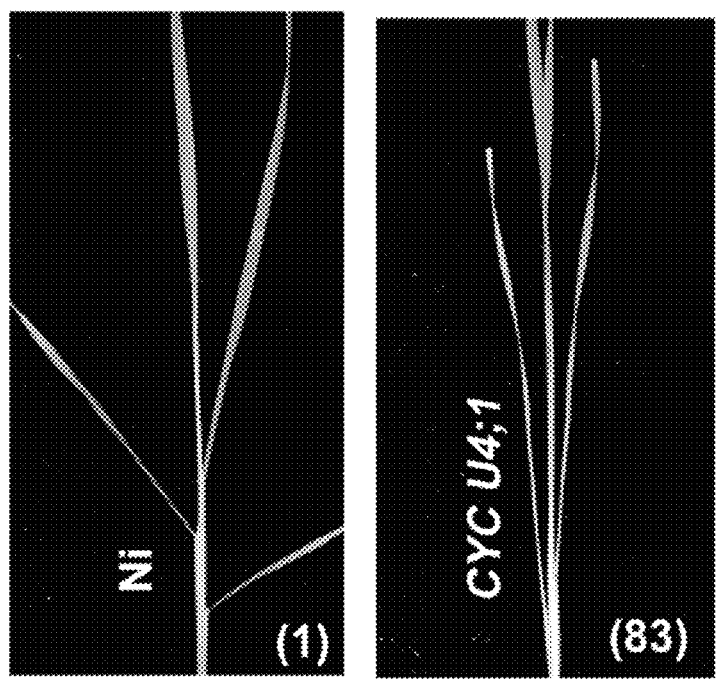

(2) By cloning the promoter and full-length CDS of CYC U4;1 to pCAMBIA1301 and transferring this into the Nipponbare, the transgenic lines obtained are characterized by having a smaller leaf-stem angle than those of wild rice (Nipponbare) as shown in FIGS. 3A and 3B. It shows that CYC U4;1 has the function of controlling the erectness development (leaf-stem angle) of the rice leaves.

Figure 4A:
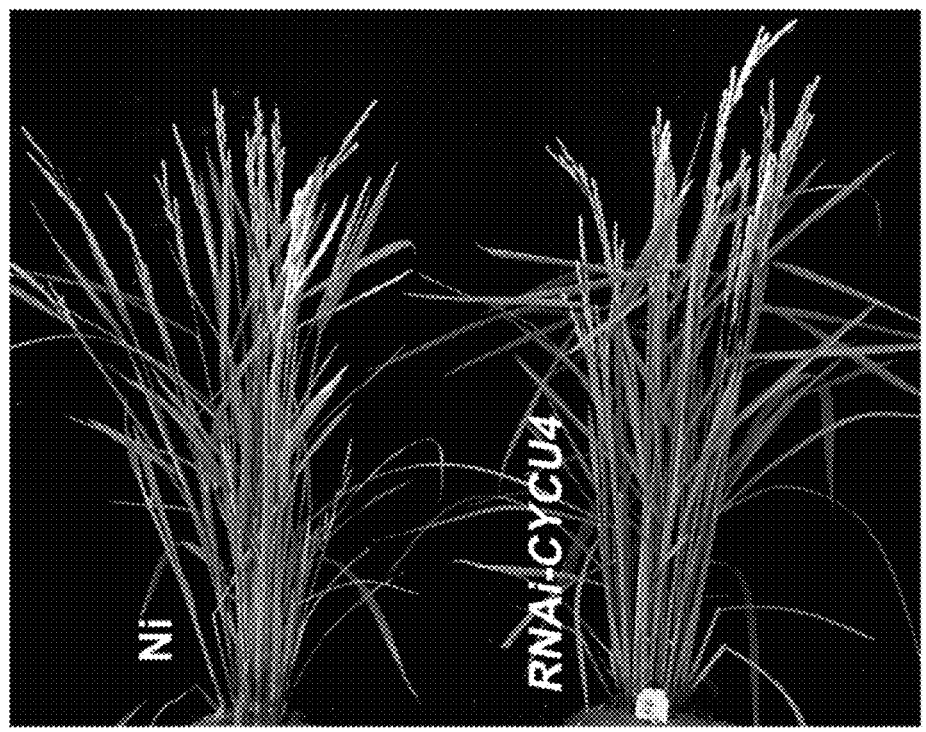
FIGS. 4A and 4B show the phenotypes and transgenic expression levels of RNAi-CYC U4;1 transgenic rice (marked as RNAi-CYCU4) in comparison to the wild type rice (marked as Ni), in which, FIG. 4A compares the phenotype and transgenic expression level of the wild type rice (Ni) and transgenic rice (RNAi-CYCU4) in the maturation stage, and FIG. 4B compares the phenotype and transgenic expression level of the wild type rice (Ni) and transgenic rice (RNAi-CYCU4) in the seedling stage.
Figure 4B:
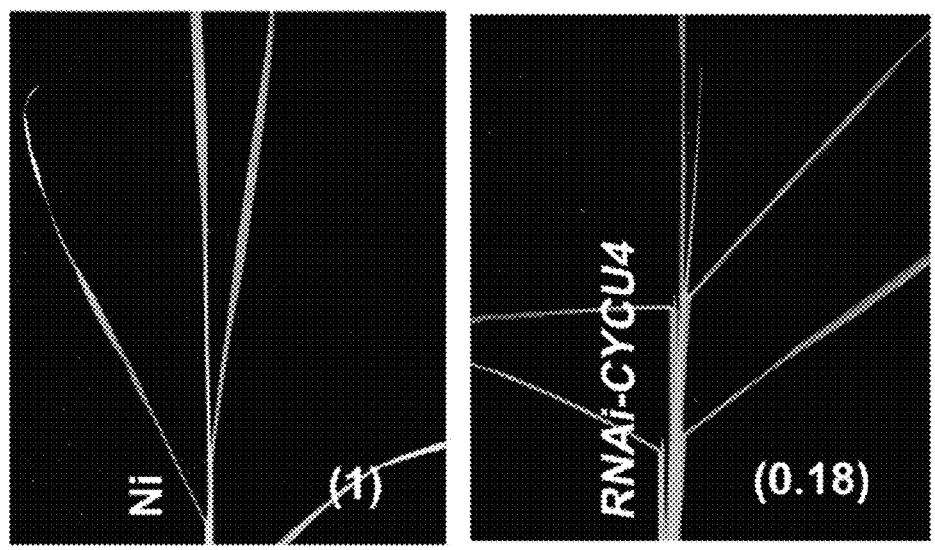

(3) By cloning CYC U4;1 (345-639 bp) to the RNAi vector pTCK303 to make an RNAi (RNA interference) experiment on the rice Nipponbare, it is found that the rice successfully transgenically transformed by RNAi has a larger leaf-stem angle than that of the wild rice (Nipponbare) as shown in FIGS. 4A and 4B.

Figure 5A:
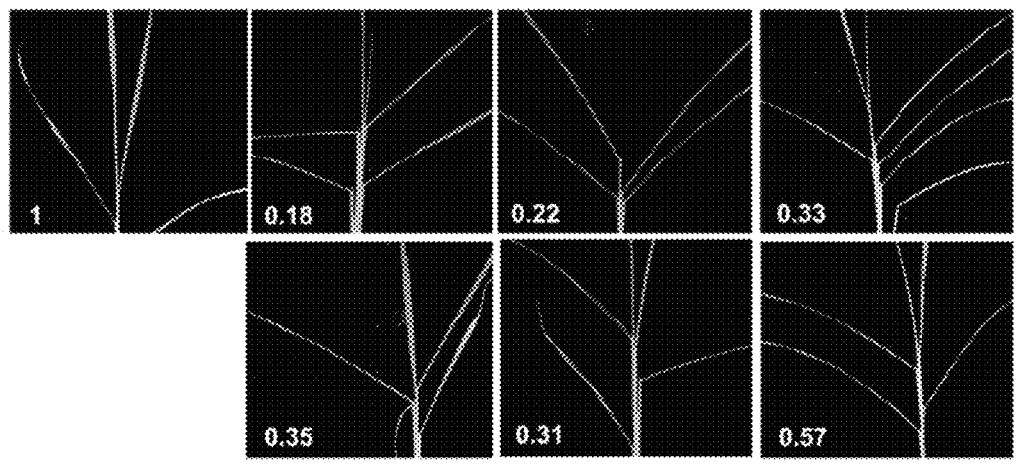
Figure 5B:
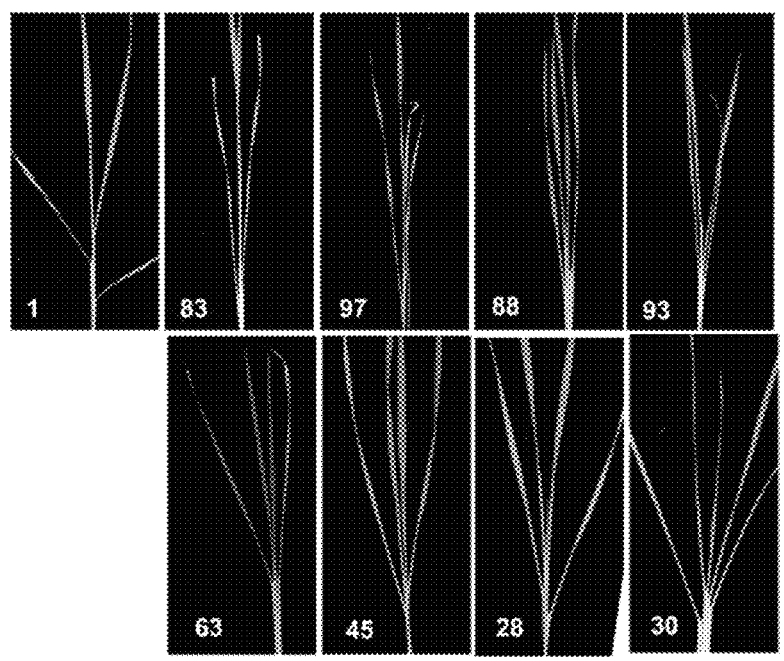

(4) By the phenotype and expression level analysis of the plurality of obtained independent pCYCU4::CYCU4;1 and RNAi-CYC U4;1 transgenic lines, it shows that the expression level of CYC U4;1 is related to the magnitude of the leaf-stem angle of the rice as shown in FIGS. 5A and 5B.

We claim:

1. A method for controlling leaf erectness development of rice plants, comprising
   cloning a cDNA nucleic acid sequence of SEQ ID NO: 2 or a truncated portion of the cDNA with a sequence of base pairs 345 to 639 of SEQ ID NO: 2 into a plant expression vector,
   genetically transforming rice plants with the plant expression vector, wherein the genetic transformation is mediated by an *agrobacterium*, and
   screening for calluses that comprise the plant expression vector, and growing the genetically transformed rice plants,
   wherein the plant expression vector comprises the cloned cDNA nucleic acid sequence.

2. The method of claim 1, further comprising
   amplifying a promoter region comprising a nucleic acid sequence of SEQ ID NO: 1, and
   cloning a fragment of the amplified promoter region into to the plant expression vector.

3. The method of claim 1, wherein the plant expression vector is constructed to have the complete cDNA nucleic acid sequence of SEQ ID NO:2.

4. The method of claim 2, wherein the plant expression vector is constructed to have the complete cDNA nucleic acid sequence of SEQ ID NO:2.

5. The method of claim 4, wherein leaf-stem angles of the genetically transformed rice plants are decreased relative to a non-transformed control plant.

6. The method of claim 1, wherein the plant expression vector is constructed to have the truncated portion of the cDNA with a sequence of base pairs 345 to 639 of SEQ ID NO: 2.

7. The method of claim 6, wherein the plant expression vector is an RNAi vector.

8. The method of claim 7, wherein leaf-stem angles of the genetically transformed rice plants are increased relative to a non-transformed control plant.

* * * * *